United States Patent [19]

Boebel et al.

[11] Patent Number: 5,454,834
[45] Date of Patent: Oct. 3, 1995

[54] SURGICAL SUTURE MATERIAL

[75] Inventors: Manfred Boebel, Otisheim; Bernd Klemm, Umkirch, both of Germany

[73] Assignee: Richard Wolf GmbH, Knittlingen, Germany

[21] Appl. No.: 29,847

[22] Filed: Mar. 11, 1993

[30] Foreign Application Priority Data

Mar. 12, 1992 [DE] Germany .............................. 9203333 U
Feb. 5, 1993 [DE] Germany .......................... 43 03 374.1

[51] Int. Cl.⁶ .................................................. A61B 17/04
[52] U.S. Cl. .......................... 606/228; 606/230; 606/231
[58] Field of Search ................................... 606/224–231, 606/78, 75

[56] References Cited

U.S. PATENT DOCUMENTS

| | | | |
|---|---|---|---|
| 3,985,138 | 10/1976 | Jarvik . | |
| 4,512,338 | 4/1985 | Balko et al. | 606/78 |
| 4,602,635 | 7/1986 | Mulhollan | 606/144 |
| 4,665,906 | 5/1987 | Jervis | 606/78 |
| 4,683,885 | 8/1987 | Hutterer et al. | 606/144 |
| 4,983,180 | 1/1991 | Kawai et al. | 606/230 |
| 5,002,563 | 3/1991 | Pyka et al. | 606/78 |
| 5,053,047 | 10/1991 | Yoon | 606/223 |
| 5,127,413 | 7/1992 | Ebert | 606/144 |
| 5,178,629 | 1/1993 | Kammerer | 606/224 |

FOREIGN PATENT DOCUMENTS

| | | | |
|---|---|---|---|
| 0331503 | 9/1989 | European Pat. Off. | 606/228 |
| 0477020 | 3/1992 | European Pat. Off. | 606/139 |
| 0494636 | 7/1992 | European Pat. Off. | 606/224 |
| 0509547 | 10/1992 | European Pat. Off. . | |
| 0559429 | 9/1993 | European Pat. Off. . | |
| 3134152 | 3/1983 | Germany . | |
| 4127812 | 2/1993 | Germany . | |
| 2157180 | 10/1985 | United Kingdom . | |
| 9014795 | 12/1990 | WIPO . | |
| WO9112771 | 9/1991 | WIPO | 606/228 |

Primary Examiner—Gary Jackson
Attorney, Agent, or Firm—Panitch Schwarze Jacobs & Nadel

[57] ABSTRACT

A surgical suture material is provided with a thread (1) and, in some cases, a needle (2) to allow formation of a knot with the greatest possible security while expending little effort, even in situations where space is limited—for example, during an endoscopic operation. The suture material has at least one inherently stable coil, loop or similar preformed feature in at least one initial preformed section (3,4) of its length. Another section of the thread (1) or an end of the thread can be threaded or guided through this preformed feature for the purpose of forming a loop and/or knot. The preformed section can take the form of a preformed feature with an approximately spiral shape, for example.

29 Claims, 6 Drawing Sheets

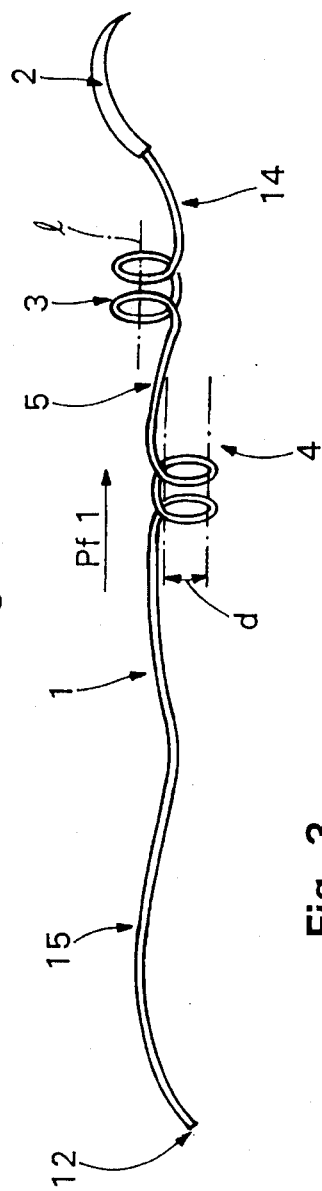
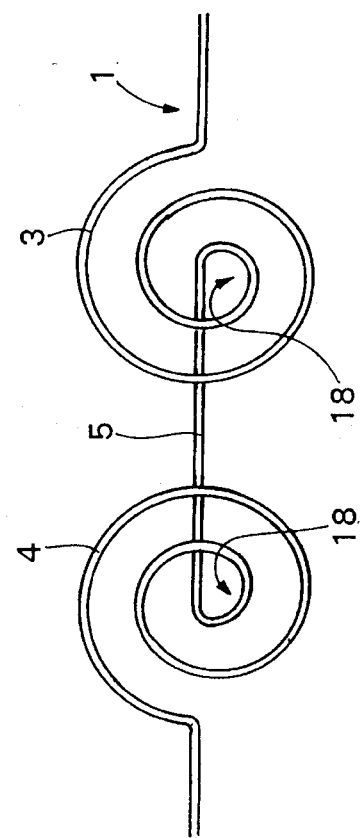
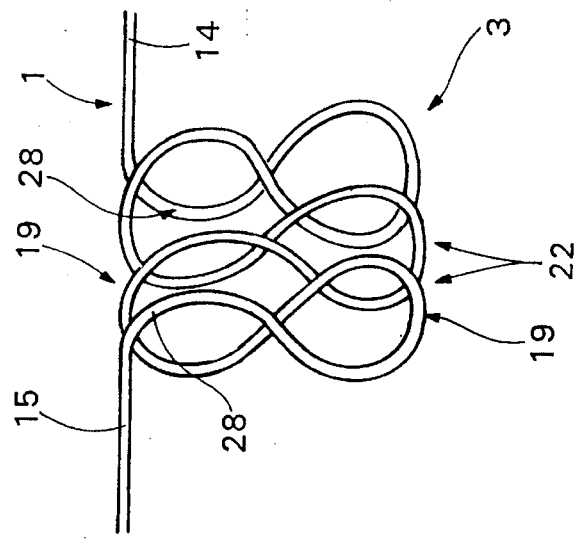
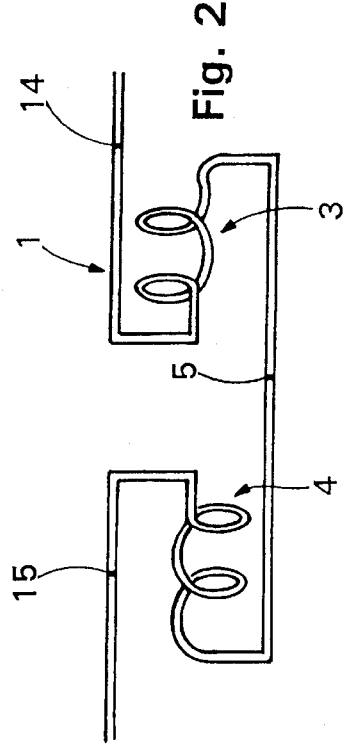
Fig. 1
Fig. 2
Fig. 3
Fig. 4

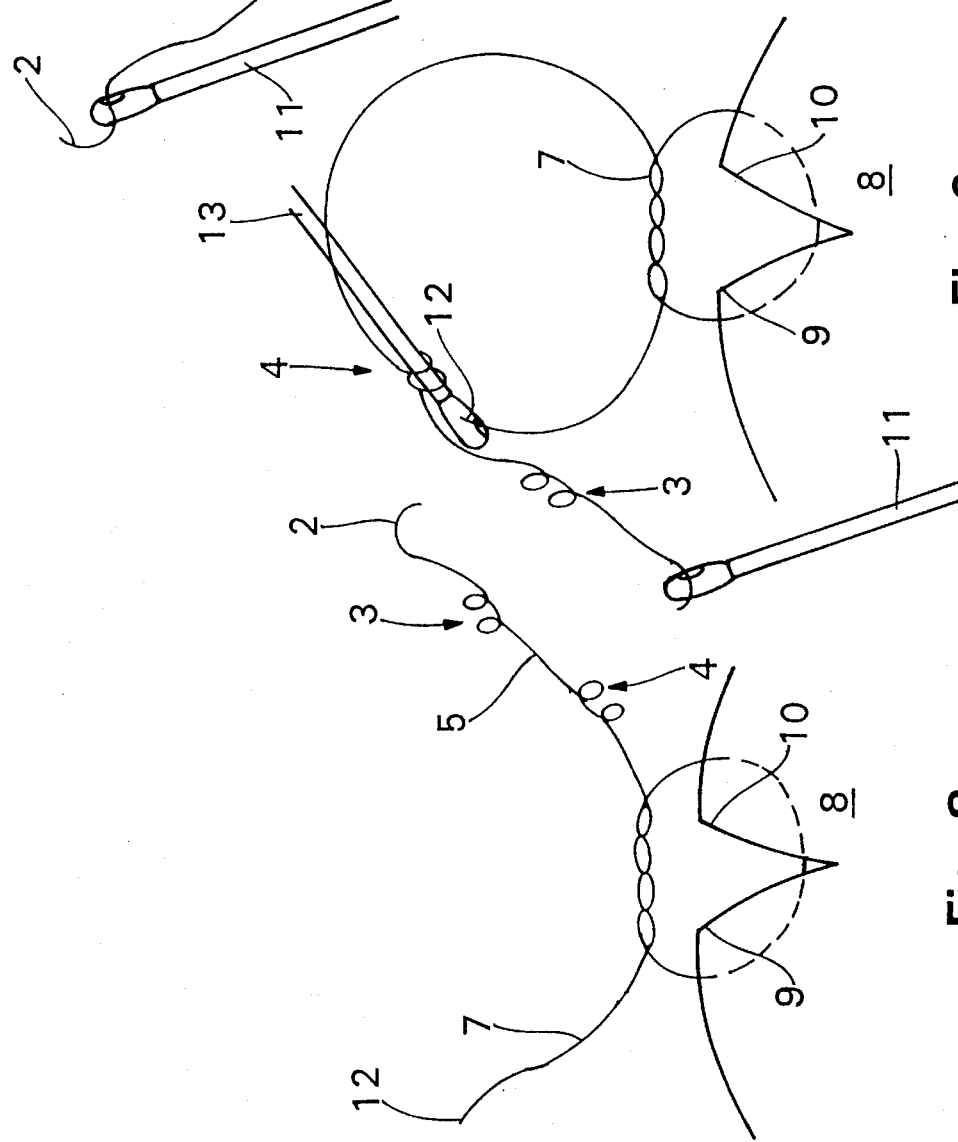

SURGICAL SUTURE MATERIAL

FIELD OF THE INVENTION

The invention pertains to a surgical suture material with a thread and, in some cases, a needle on at least one end of the thread.

BACKGROUND OF THE INVENTION

Surgical suture material is available as a thread which is cut to length and prepackaged. In most cases, a surgical needle is firmly attached to one or both ends of this thread. Suture material of this type is sometimes sold as a separately packaged single thread. In this case, the thread is usually coiled in a space-saving manner within the package.

The thread of a surgical suture material which consists of synthetic monofilament material is especially likely to be relatively hard and elastic, so that even after being subjected to elongation, it returns in an uncontrolled manner to an indefinite approximation of its previous shape. This can make it more difficult to manipulate the above-mentioned suture material, especially in situations where space is limited.

Suture material of this type is also used in intracorporal endoscopic operations, in which the functional end of the required surgical instruments and the surgical suture material are inserted into the body of the patient via individual trocar cannulae. In order to provide the tissue with a surgical suture even in operations of this type, and in order to use instruments to apply an intracorporal surgical knot in this situation, the tissue which is to be sutured is pierced with the needle, and the attached thread is grasped with a thread holder or needle holder. The thread can then be placed around a second thread holder or needle holder, which executes a circular motion and guides the thread with its shank in such a way that the thread is wound in a spiral around the jaw parts of the thread holder or needle holder. The opposite end of the thread is then grasped with these jaw parts and drawn through the spiral winding, If each end of the thread is now pulled with a thread holder or needle holder, the so-called base knot is formed. In order to hold this base knot in its position or secure the tension once it has been created, a so-called finishing knot is tied tightly over the base knot in the same manner.

When the abdomen is open and the threads of the surgical suture material are sufficiently long, it is relatively simple to produce a surgical knot in the manner described above. However, this technique is very difficult to perform when the abdomen is closed and the instruments are inserted via trocar cannulae, because the threads frequently slip off the thread holder or needle holder and return to their original position. The reason for this is the above-mention hardness and elasticity of the thread and/or the vertical position of the instruments which often occurs in intraabdominal endoscopic operations. The instruments which are inserted into the abdomen via trocar cannulae can only be repositioned to a limited degree to counteract the slipping motion of the thread, especially since endoscopic operations allow only very limited space for moving the instrument to follow the thread.

In the case of extraordinarily stiff monofilament thread material, as is frequently used in endoscopic operations, it can be especially difficult even to wind the thread of the suture material around the jaw parts of the instrument for the purpose of tying the knot. Even if this is accomplished, the thread must often be pulled tight with the instruments, in order to prevent it from slipping off the thread holder or needle holder. However, this tensile load on the thread can cause a tearing of the tissue which is to be sutured.

Therefore, an especially important object is to create a surgical suture material whose thread can be quickly and securely formed into a surgical knot in the smallest possible space. The suture material provided by the invention should especially facilitate the formation of a secure knot and allow this to be performed with the least possible effort.

SUMMARY OF THE INVENTION

The solution to this problem, as provided by the invention, consists especially in the fact that the suture material has at least one inherently stable coil, loop or similar preformed feature in at least one initial preformed section of its length, and that another section or end of the thread can be threaded or guided through this preformed feature for the purpose of forming a loop and/or knot. The suture material provided by the invention has at least one coil, loop or similar preformed feature in at least one initial preformed section of its length. The jaw parts or arms of a thread holder or needle holder, for example, can also be guided through this preformed feature. After these jaw parts have been passed through the preformed feature, the opposite end of the thread can be grasped with the thread holder or needle holder and guided or drawn through the preformed feature, so that the base knot or finishing knot of a surgical knot is formed. Instead of guiding the jaw parts of the instrument through the preformed features of the suture material, it is also possible to thread one end of the thread through these features, for example. With the help of the preformed section of the suture material provided by the invention, it is possible to form a loop or knot in a simple manner. This can be performed without requiring the thread to be wound around the jaw parts with circular motions of the thread holder or needle holder, which requires an especially great amount of effort in limited spaces and is sometimes difficult to accomplish at all.

It is indeed conceivable that the suture material provided by the invention could have such coils, loops or similar preformed features across practically its entire length. In the preferred embodiment, however, only one section or possibly multiple sections of the suture material are preformed in this manner.

For example, one embodiment of the invention which is especially simple and inexpensive to produce provides for the preformed section of the suture material to be formed as an approximately spiral preformed feature. The helically wound preformed features of a spirally preformed section of the suture material make it especially simple to thread one of the two ends of the thread of this suture material through the preformed feature, for example.

In order to facilitate not only the formation of the base knot, but also the formation of the finishing knot, it is useful for the suture material to have multiple—preferably two—preformed sections at a distance from one another, and for the spiral preformed features of these sections to have opposing directions of rotation. In an embodiment of this type, the base knot and finishing knot can be executed as a sailor's knot, in which one end of the thread is wrapped once forward and once backward around the other section of the thread.

On the other hand, it may be desirable to form only a so-called granny knot, in which one of the two sections of the thread is knotted twice around the other section. This knot is characterized by a certain ability to slip. In this case, only one spiral section is needed, provided that at least the preformed section of the suture material is made of an elastic material. The reason for this is that after the base knot has been tied and the ends of the thread have been drawn tight, the preformed section returns to its spiral form, because of the elasticity of the suture material in this section. As a result, the finishing knot can also be formed by drawing the opposite end of the thread through the preformed feature.

It is advantageous for each spiral preformed feature of at least one section—but preferably two sections—of the suture material to have multiple—preferably two—coils or similar preformed features. The base knot and, if desired, the finishing knot can thus be formed into a double-wound, so-called surgical knot.

In order to be able to form a knot in a simple manner with the suture material provided by the invention, and in order to be able to guide the arms of a thread holder or needle holder through the preformed features of this suture material, it is practical for the inside diameter of each spirally preformed section of the suture material to correspond to the outside dimensions of a surgical thread holder in the region of the jaw parts of the thread holder, for the purpose of guiding this thread holder through the preformed features.

One embodiment of the invention which is of particular significance provides for the suture material to have at least two adjacent coils, loops or similar preformed features in at least one initial preformed section of its length. These preformed features have opposing directions of rotation. This refinement also provides that another section or end of the thread can be guided through at least one of these coils or similar preformed features for the purpose of forming a loop or knot, and that the central axes of these adjacent, counter-rotating coils or similar preformed features lie at a distance from one another. In order to be able to form a knot or loop in a simple manner using the suture material provided by the invention, the opposite end of the thread can be drawn through at least one of the coils or similar preformed features, for example. A special advantage of this embodiment of the invention is that the opposing directions of rotation of its coils, loops or similar preformed features counteract an undesirable twisting of the thread. The result is a tensionless knot and no loosening of the tied knot, as can occur with twisted threads.

In fact, when the end of a thread is guided through a preformed coil and the knot is drawn tight, an axial twisting of the thread can develop. This twisting can impair the correct positioning of the knot in the region where the knot is seated, thus impairing the holding function of the knot, in turn. This is especially likely to occur when using stiff thread material and when tying knots in tight spaces. When tying surgical knots, the twisting of the thread in the region where the knot is seated can even cause the formation of "air loops", so that even the base knot can not adequately perform its holding function. Slippage of the knot, which can possibly occur later, could lead to a dehiscence of the adapted tissue and/or to secondary bleeding where blood vessels are involved. This deleterious effect on the security of the knot becomes more severe as the thread becomes shorter.

Because this disadvantageous effect of the twisting of the thread can hardly occur in this embodiment of the invention, it is possible to create a tensionless knot, even with very short threads. Because the coils or similar preformed features of the suture material provided by the invention are adjacent to one another, the suture material can also be made relatively short in its preformed section. Both of these advantages fulfill the requirement of simple manipulation—for example, when the thread material must be inserted through the trocar cannula into the body of the patient within the context of an intracorporeal operation. At the same time, this relatively short formation of the suture material provided by the invention makes it unnecessary to exert a great amount of force in drawing the knot tight. The reason for this is that in the case of longer threads, the task of guiding the end of the thread through the loop and drawing the knot tight sometimes requires a great amount of space for moving the instruments or even repeatedly grasping the thread. The central axes of the adjacent, counter-rotating coils or similar preformed features lie at a distance from one another. In order to form a sailor's knot, one end of the thread is thus initially drawn through only one coil of the preformed section, and the base knot is formed. The finishing knot is then tied in the opposing direction, possibly with the help of the other coil, which has an opposing direction of rotation.

On the other hand, if it is desirable to provide the knot with a relatively loose seat, the same coil must be used for both the base knot and finishing knot, in order to form a granny knot.

In order to be able to effectively guide the jaw parts of a thread holder—or even just an end of the thread—through the coils or similar preformed features of the suture material, it is practical for each pair of adjacent coils or similar preformed features to be arranged in approximately the same plane, with opposing directions of rotation.

One preferred embodiment of the invention provides for each pair of adjacent coils or similar preformed features with opposing directions of rotation to form a preformed feature with the approximate shape of a figure eight or double loop. A figure-eight-shaped double loop of this type requires a relatively short thread length and simplifies the manipulation of the suture material provided by the invention to a considerable degree.

In situations involving two adjacent coils or similar preformed features with opposing directions of rotation, these coils or similar preformed features can cause a twisting of the thread. In order to counteract this twisting, it is advantageous for the thread segment which enters one of the coils and the thread segment which exits the other coil to lie on opposite sides of their common transition section. The "thread segment which enters one of the coils" and "the thread segment which exits the other coil" are intended here to mean the coil segments of the respective coils or similar preformed features which are positioned in front or back with respect to the same thread direction. The material segment which is provided between the adjacent coils is described here as the "transition section".

For all practical purposes, twisting of the suture material according to the invention is completely prevented when each coil or similar preformed feature of the preformed section with a given direction of rotation is paired with another coil or preformed feature with an opposing direction of rotation.

It is useful for the preformed section of the suture material to have more than two adjacent coils or similar preformed features, for each pair of adjacent preformed features to have opposing directions of rotation, and for the central axes of the preformed features with the same direction of rotation to be arranged in an approximately coaxial relationship. In this embodiment, the preformed section of the suture material has at least two overlapping coils, loops or similar features with the same direction of rotation, adjacent to another preformed feature with the opposing direction of rotation. If one end of the thread is then drawn through the two coils which have the same direction of rotation, it is possible to form a double winding of the type needed for the so-called surgical knot, for example.

An especially simple embodiment of the invention provides for the preformed section of the suture material to have three adjacent coils or similar preformed features, of which one preformed feature with a given direction of rotation is positioned between two preformed features with the opposing direction of rotation. Using an embodiment of this type, it is possible to form a surgical knot in which a double-wound base knot can be formed by means of the two coils or similar preformed features which are arranged in an approximately coaxial relationship to one another and have the same direction of rotation. A simple finishing knot can be formed by means of the coil with the opposing direction of rotation.

When using the suture material according to the invention, the position of the preformed section in its angular relationship to the exiting thread or adjacent thread segment can be made clearer, and the manipulation of this suture material can be made even simpler. In order to accomplish this, it is useful for at least one—but preferably both—of the segments of the suture material which are adjacent to the preformed section to be angled in a transverse, and ideally perpendicular, relationship to the plane formed by the adjacent coils or similar features and/or the double loops.

The embodiment of the suture material according to the invention, as described above, with its double loops in the form of a figure eight, represents the preferred embodiment. The reason for this is its simple form and manipulation, and the ability to form a secure, tensionless knot, even with very short threads. However, a further embodiment of the invention—which is of independent significance is also sought—also provides for two adjacent coils or similar preformed features or two adjacent preformed sections with opposing directions of rotation to be arranged in an eyeglass shape in relation to one another. Each of these two adjacent sections can also be preformed as spirals. In at least one eyeglass-shaped arrangement of two adjacent coils or similar preformed features with opposing directions of rotation, a twisting of the suture material is counteracted when the thread segment which enters one of the coils and the thread segment which exits the other coil are arranged on the same side of their common transition section.

After forming the base knot, in order to be able to wind the finishing knot in the opposing direction to form a sailor's knot or in the same direction to form a granny knot, and in order to be able to recognize each of the coils or similar preformed features with the corresponding direction of rotation, for example, it is advantageous for the preformed sections of the suture material to display a marking dye, marking coating or similar form of marking. This applies especially to the coils or similar preformed features with the same direction of rotation and/or the segments of the suture material which are provided between two adjacent preformed sections and/or the segments of the suture material which lead to and/or from the preformed features. For example, it is possible for only the the coils or preformed features with one direction of rotation to display a marking of this type. As an alternative, it is possible to mark the coils with one direction of rotation as well as the coils with the other direction of rotation, in which case the coils or preformed features should display certain distinct markings, depending on their direction of rotation. In a similar way, it is also advisable to color the segment of the suture material which is provided between two adjacent preformed sections and/or the segments of the suture material which lead to and/or from the preformed features. These colors should differ from the colors of the coils or preformed sections.

The easy manipulation and simple formation of a knot with the suture material provided by the invention can be further facilitated by arranging the longitudinal axis or axes of the preformed section or sections in the same direction as the longitudinal axis of the suture material. In this way, each preformed section of the suture material forms a thread opening which is arranged in a practically transverse relationship to its longitudinal axis. Both jaw parts of a conventional thread holder or needle holder can be guided in a simple manner through this thread opening, or one or both ends of the suture material can be threaded in a simple manner through this thread opening.

The preformed section of the suture material according to the invention can be produced by an appropriate coating or pasting of the suture or thread material, soaking in a form-stabilizing solution, or similar treatment and then given the desired form, so that the immediately adjacent sections of the preformed section of the suture material according to the invention adhere to one another, for example. In an embodiment of this type, only two preformed sections may need to be provided in order to allow the base knot and finishing knot to be formed in a simple manner, for example.

However, a further embodiment of the invention provides for at least the preformed section of the suture material to consist of an elastic material. Because at least the preformed section of the suture material provided by this preferred embodiment of the invention consists of an elastic material which returns to its original preformed shape in the relaxed condition, the coils or similar preformed features of this preformed section are formed anew after the base knot has been formed and the tension on the thread has been relaxed. These coils or similar preformed features can thus be used for the finishing knot, as well. Furthermore, the suture material can first be drawn through a trocar cannula or through the tissue which is to be sutured, after which at least sections of it can assume the preformed shape which is desired for tying the knot—for example, a spiral shape. The suture material provided by the invention can therefore be used not only for operations on the open abdomen and for skin sutures, but also for intracorporeal endoscopic operations in particular.

In order to also be able to combine the advantages of different suture or thread materials, and in order to be able to form a knot with the help of an inelastic thread material, for example, a further embodiment of the invention which is of particular importance provides for the preformed section or sections of the suture material to take the form of a piece or pieces which are connected—preferably in a detachable manner—to the adjacent thread segment or segments. This connection is preferably accomplished by means of a plug connection, clamp connection or similar connecting element. In this refined embodiment of the invention, the surgical suture material can be formed in two or three parts. For example, it can have a section which has been preformed for the purpose of forming knots and/or loops and which preferably comprises elastic material. At least the free end of this preformed section can be connected—preferably in a detachable manner—with a thread segment comprising elastic or possibly even inelastic material. The connection between one of the two ends of this preformed section and the adjacent thread segment or another preformed section can be accomplished by means of a plug connection, clamp connection or similar connecting element.

In cases of special applications, it can be useful for the thread and/or the preformed section or sections of the suture material to be formed of a memory metal—especially a nickel-titanium alloy. The entire suture material can essentially be formed of a memory metal thread of this type. As an alternative, the suture material provided by the invention can have only a preformed section of a memory metal alloy of this type, which is connected in a detachable manner, for example, with the conventional thread. In an embodiment of this type, the suture material provided by the invention can be inserted in an elongated form through a trocar cannula or similar device into the body, for example. Inside the body, the section comprising memory metal can then be placed in its inherently stable, preformed shape by the effect of heat.

Suitable thread materials for use in the sutures of the present invention will be recognized by those skilled in the art and include both monofilament and multifilament threads. Examples of suitable elastic thread materials include those made of synthetic fibers, such as polyesters (e.g., Dacron, Terylene, Trevira), polyamides (e.g., nylon, Perlon), polyolefins (e.g., polyethylene or polypropylene), polydioxane, polyglyconates, etc.; animal gut, such as cat gut or chromated catgut; and metals, such as steel, tantalum, silver, shape-memory-metal, etc. Polyfilaments of jacketed filaments, such as twisted polyamide with polyamide jacket (e.g., SUPRAMID) may also be used. Examples of suitable inelastic thread materials include flocked or twisted threads of synthetic fibers (e.g., polymers and copolymers of glycolic acid) or natural fibers (e.g., silk, linen or wool), as well as laminar turned threads of collagen, for example, such as laminar, turned catgut (e.g., SOFTCAT).

BRIEF DESCRIPTION OF THE DRAWINGS

The foregoing summary, as well as the following detailed description of presently preferred embodiments of the invention, will be better understood when read in conjunction with the appended drawings. It is understood, however, that this invention is not limited to the precise arrangements illustrated.

FIG. 1 is a side view of a surgical suture material with a thread connected to a needle; the thread displays multiple inherently stable coils in each of two preformed sections which lie at a distance from one another, forming a spiral preformed feature;

FIG. 2 is a surgical suture material, similar to the one in FIG. 1;

FIG. 3 is a surgical suture material whose thread displays two spirally preformed sections, which also lie at a distance from one another;

FIG. 4 is a surgical suture material whose thread displays multiple adjacent coils, loops or similar preformed features within a preformed section of its length; these preformed features display opposing directions of rotation, and each pair of adjacent preformed features with opposing directions of rotation form a double loop with the approximate shape of a figure eight;

FIGS. 5 to 10 show the placement of a single suture with a suture material similar to the one shown in FIG. 1; this suture material is preformed as a spiral in two sections of its length which lie at a distance from one another;

DETAILED DESCRIPTION OF PREFERRED EMBODIMENTS

Figure 5:
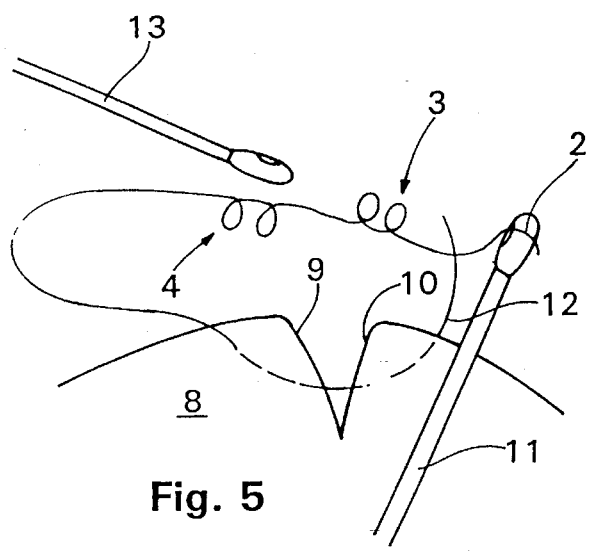

Additional features of the invention can be derived from the following description of sample embodiments of the invention, in connection with both the claims and the drawings. An embodiment of the invention can implement each of the individual features alone or in combination.

FIG. 1 depicts a surgical suture material with a thread 1, one end of which is connected in a molded manner to a needle 2. In order to make the formation of knots considerably easier, even in situations where space is limited, the thread 1 of the suture material has two preformed sections 3,4 along its length. Each of these preformed sections assumes a spiral or helical shape for the purpose of guiding the two jaw parts of a thread holder or needle holder (not shown here) or one end of the thread through it. The inside diameter d of these sections 3,4 corresponds to the outer dimensions of a thread holder or needle holder in the region of its jaw parts, for the purpose of guiding this holder through these sections along the central or longitudinal axis L of the preformed section.

In principle, the sections 3,4 can be arranged at any desired location along the length of the suture material. However, it is preferable to arrange these sections 3,4 in the region of the thread 1, and especially in the region of one of the two ends of the thread, as shown here.

The entire thread 1—and thus its sections 3,4—are made of an elastic material, so that the thread returns to the original form shown here, even after the thread 1 has been stretched as it is drawn through a trocar cannula or the tissue to be sutured.

As can be recognized easily in FIG. 1, the preformed sections 3,4 which are arranged on opposite sides of the suture material lie at a distance from one another and have opposing directions of rotation. After both arms or jaw parts of a thread holder or needle holder have been guided through the spiral preformed feature of section 4, the opposite end of the thread 12 can be grasped and thus drawn through this section 4 in such a way that the base knot is formed. Once the base knot has been formed, sections 3,4 return to the original form shown here. In order to also form the finishing knot over the base knot, the two arms of the thread holder or needle holder are then guided through section 3—again in the direction of the arrow Pf1—and the end of the thread 12 is then grasped and pulled through the spiral preformed features of this section 3. Because of the opposing directions of rotation of these sections 3,4, the base knot and finishing knots are tied in the form of a sailor's knot. In this type of knot, the two loops of the individual knots—which are similar, but lie in opposing positions in relation to one another—will be drawn increasingly tighter as the thread is subjected to greater tension.

If the knots are intended to take the form of double-wound surgical knots, it is useful for each of the sections 3,4 to have spiral preformed features—preferably with two coils, as shown here. In order to be able to recognize the sections 3,4 with the spiral or helical preformed features, even when the thread is stretched straight, it is advantageous for these sections—and in some cases, the section 5 which is arranged between them and/or each segment of the suture material which leads to or from a preformed section—to display a marking dye, marking coating or similar form of marking. It is especially useful for the markings of sections 3,4 and the other marked sections of the thread to differ from one another.

For example, in the embodiment of the suture material depicted in FIG. 1, it is possible for the preformed section 3, as well as the thread segment which leads to this section 3 and is adjacent to the needle 2, to display a marking of a certain color, which indicate the threading or insertion direction of this section 3. Thread section 5 and section 4 would bear a different indicator marking, or none at all, In the embodiments represented in FIGS. 11 and 12, on the other hand, it is sufficient to use a color to mark only those coils 19 which are oriented in one direction of rotation and the thread segment which is adjacent to these coils, in order to indicate the threading or insertion direction of the loop sections of the double loops 22 which are oriented in both directions of rotation.

The surgical suture material can be made of various materials, which may also vary across its length. For example, the thread can consist of an inelastic material, in which case the preformed sections of the thread are formed by an appropriate adhesive or similar coating of the adjacent coils. It is also possible for the thread 1 of the suture material to be made of a memory metal alloy which returns from an elongated shape to its original condition, with its sections of spiral preformed shapes, in a manner which is dependent on temperature. It is useful for the thread 1 of the surgical suture material to consist of an elastic material in at least the region of the spiral preformed sections. The spiral preformed features of the thread in these sections allow a trouble-free grasping by the two jaw parts of a conventional thread holder or needle holder, so that the opposite end of the thread can be grasped with these jaw parts and drawn through the preformed section.

The troublesome task of winding the thread around the thread holder or needle holder can be eliminated, and it is no longer necessary to maintain tension on this wrap around the jaw parts of the thread holder or needle holder in order to prevent it from slipping off the thread holder or needle holder. This can also reduce the risk of injury with the suture material provided by the invention. The loop needed for forming the knot can be arranged in a space-saving manner in the immediate vicinity of the point where the knot will later be seated. With the suture material provided by the invention, the desired knot can also be formed by means of simple, conventional thread holders or forceps, without requiring circular motions of these instruments for the creation of the loop.

The method for forming a suture with a finishing knot with the suture material depicted in FIG. 1 is described below, with the help of FIGS. 5 through 10. In FIGS. 9 through 10, the tissue which is to be joined by the suture is identified by the number 8. The edges 9 and 10 of an incision with a V-shaped cross section, shown here in a highly schematic representation, shall be joined to one another by the suture. In the position shown in FIG. 5, an initial needle holder 11 has been used to guide the needle 2 with the attached thread 1 through the tissue 8, first through edge 10 and then through edge 9. The thread 1 is pulled so far through the site to be sutured that the end of the thread 12 protrudes from the tissue 8 with just enough length for the formation of a knot. This end of the thread is the end of thread segment 15 (FIG. 1), which is not preformed and is adjacent to section 4 on the end of the suture material which is directed away from the needle 2.

Figure 6:
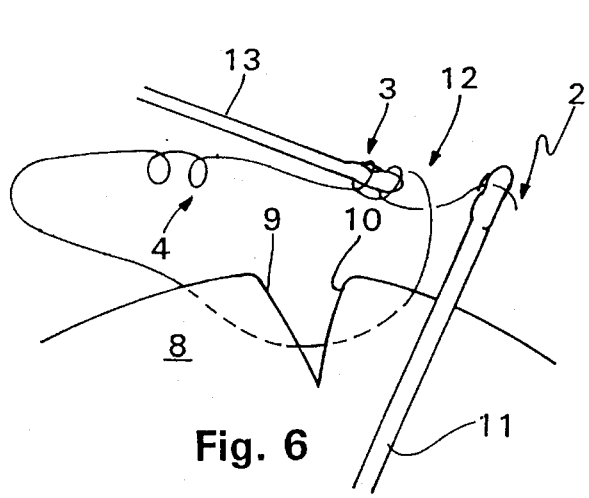
Figure 7:
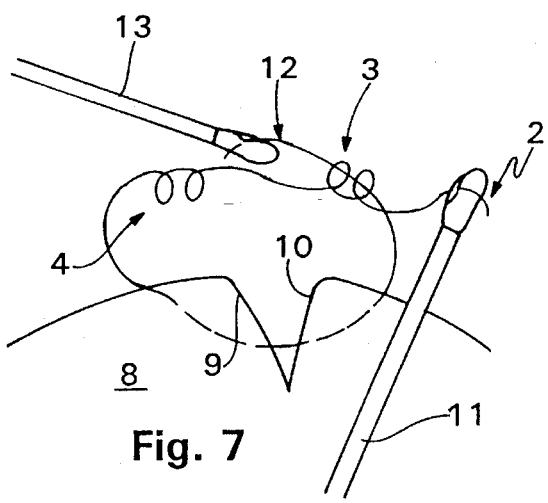

As shown in FIG. 6, grasping is then performed with a second needle holder 13 from the thread segment 5 which is directed away from the needle 2, through the two spiral preformed features of the initial preformed section 3, and the free end of the thread 12 is picked up with this second thread holder 13. As shown in FIG. 7, the end of the thread 12 is then drawn back through the spiral preformed features of section 3 with the needle holder 13, thus forming the base knot.

The finishing knot which is required for securing the surgical knot is formed as follows. The process described above is repeated with the spiral preformed features of the preformed section 4, as depicted in FIGS. 8 through 10. FIG. 8 clearly shows that the base knot has been formed and how the free end of the thread 12 must now be drawn through the spiral preformed features of the preformed section 4, for the purpose of forming the finishing knot in the opposite direction.

In accordance with FIG. 9, the second needle holder 13 is now guided through the spiral preformed features of the preformed section 4, in the direction of the initial preformed section 3. The free end of the thread 12 is then grasped with the second needle holder 13 and drawn back through the spiral preformed features of section 4. The surgical knot is then completed by drawing apart the end 12 and the end of the thread which is attached to the needle 2, as indicated in FIG. 10. After the thread has been cut off at the knot, additional single button sutures can be performed with this thread 1 of the suture material, in the same way as described above.

The spiral preformed features of sections 3,4 are formed by a plastic shaping process from a thread 1 which is not preformed. The shaping process produces a form which allows the spiral preformed features to be drawn through the tissue 8 without any trouble and to stretch into an approximately straight form when being drawn through in this manner. As a result, the punctures are not widened unnecessarily. After being drawn through the tissue 8, the thread 1 returns to its preformed shape in the region of sections 3,4, so that their spiral preformed features reappear. This effect also occurs when the base knot and finishing knots of a surgical knot are pulled together. The required number of spiral windings in the preformed sections 3,4 depends on the desired knot.

As a rule, the knot-forming procedure depicted in FIGS. 5 through 10 will only be advisable and/or unavoidable in a surgical field which is difficult to access, or when an adequate view into the surgical field is not possible. It will usually be sufficient to draw the segment of the suture material which is connected to the needle 2, and which displays appropriate dimensions, through the tissue 8 until it reaches the initial preformed section 3. The base knot and finishing knot are then formed by using the end of the thread which is connected to the needle 2.

Here it is especially advantageous to thread only the appropriate end of the thread through the preformed features of the preformed section 3,4, instead of grasping through these coils or similar features with the jaw parts of a needle holder or thread holder. Otherwise, the entire length of the thread 1 of the suture material—as depicted in the drawings—must be drawn through the tissue 8. This includes a large section of the thread segment 7 which is not preformed. The reason for this is that the needle holder must be guided through the coils or similar preformed features of the preformed sections 3,4 from an unfavorable angle—namely from the side of the wound bed. If the preformed thread section is not to be drawn through the wound, the needle holder must still be guided through the preformed sections 3,4 from the side of the wound bed. Both of these procedures can make it more difficult to manipulate the suture material, for reasons which include the great amount of space required for executing the instrument motions. Even when the preformed sections are positioned quite favorably, an especially great amount of space is required for drawing the knot tight when the thread 1 is formed with two coils which lie at a distance from one another and display multiple windings and an appropriate diameter, corresponding to the jaw parts of the instrument. If the surgical field does not provide the space needed for drawing the knot tight, the knot must be drawn tight in stages, which may make it necessary to grasp the thread repeatedly.

Figure 14:
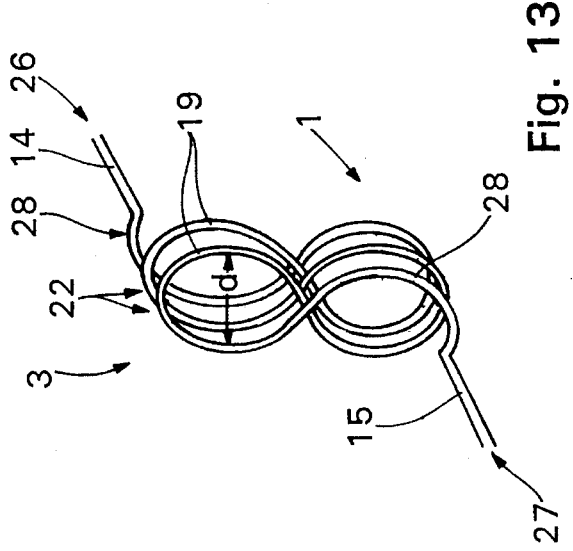
FIG. 14 is a surgical suture material whose thread segments outside the preformed features are angled in the direction of the adjacent preformed section.

In a surgical field where space is limited, a troublesome guidance of the jaw parts of the instrument through the loops from the side of the wound bed can also be avoided by providing for the thread sections which lead to and/or from the coils or similar preformed features and are not preformed to be diverted in the direction of the adjacent preformed thread sections. The coils or similar preformed features whose diameter corresponds to the jaw parts of the instrument are thus inclined by approximately 180° in their plane, which lies approximately perpendicular to the longitudinal axis of the thread. This is depicted in FIGS. 2 and 14, for example.

Here the thread 1 depicted in FIG. 2 is formed in a manner similar to the suture material in FIG. 1. The spiral preformed sections 3,4 with opposing directions of rotation are separated from one another by a thread segment 5 which consists of straight thread pieces and is provided here with right angles along its length. The thread segments 14,15 which exit sections 3,4 extend in opposite directions. This can facilitate the guidance of the jaw parts for the purpose of grasping and drawing the thread end through the position of the thread holder or needle holder instrument.

A preformed section which runs back in the opposite longitudinal direction of the thread 1 in this manner can even reduce the space required for the instrument motions which are depicted in FIGS. 5 through 10, for example, by now causing the guidance of the jaw parts of the instrument through the preformed features to be performed in the direction of the wound bed. This is helpful in facilitating the instrument position in endoscopic operations, which is usually vertical.

Here it is no longer necessary to draw the preformed section of the thread far away from the wound bed with the help of a second needle holder, in order to guide the jaw parts of the initial needle holder through the preformed features in the proper direction. This can be seen clearly in FIGS. 6 and 9, for example.

On the other hand, if only the end of the thread which is to be knotted—and not the needle holder—is drawn through the preformed loops or similar preformed features, an even smaller thread segment is needed for tying the knot. As a result, the knot can be formed by drawing tight a relatively short piece of thread, even in situations where space is limited. The end of the thread which is pushed through the spiral preformed features, for example, is grasped on the other side and pulled tight for the purpose of forming the knot. In this preferred procedure, the diameter d of the inherently stable coils or similar preformed features must be just slightly greater than the diameter or thickness of the thread material. In this preferred procedure, the guidance of the thread 1 is not performed from the side of the wound bed, but from the side located away from the wound bed. This eliminates the troublesome guidance of the jaw parts of the instrument from an unfavorable guidance angle on the side of the wound bed, for example.

Figure 15:
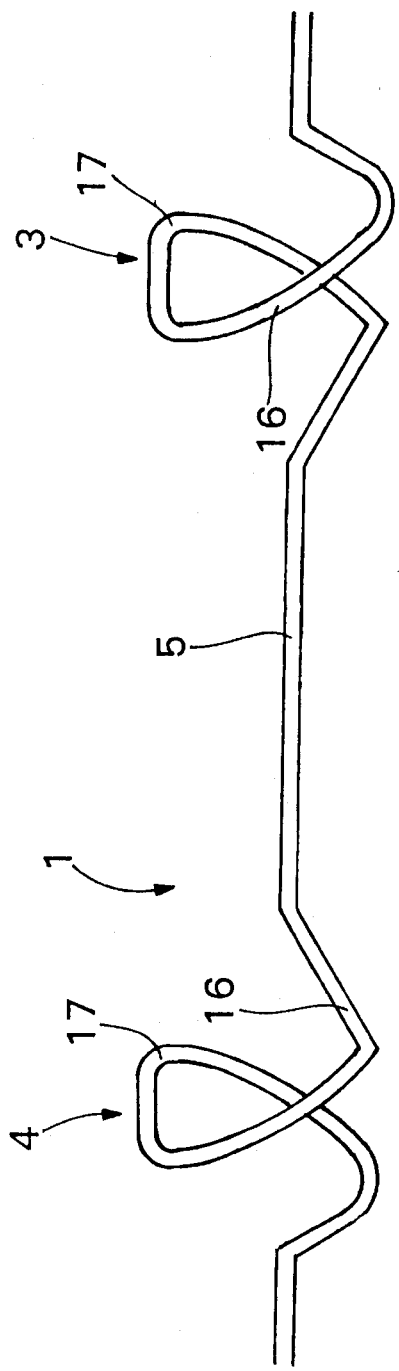
FIGS. 15 and 16 are two additional embodiments of a surgical suture material, in which the coils, loops or similar preformed features of the two preformed sections—which lie at a distance from one another—are essentially triangular in shape.
Figure 16:
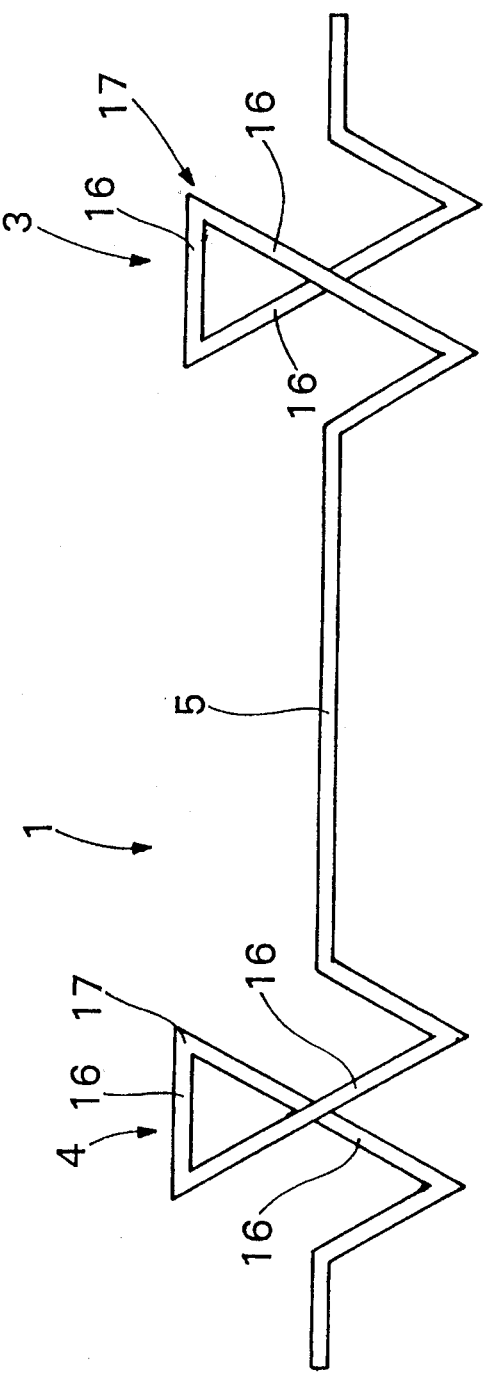

FIGS. 3, 15 and 16 depict other embodiments of the suture material provided by the invention, in which the thread 1 also displays two preformed sections which lie at a distance from one another and contain appropriate preformed features which are intended to facilitate the formation of a knot in situations where space is limited, in accordance with the invention.

The thread 1 of the suture material depicted in FIG. 3 displays two spiral preformed sections 3,4 with spiral windings wound in opposite directions. These preformed sections lie at a distance from one another, in an arrangement resembling the shape of a pair of eyeglasses. By simply threading one end of the thread through the center 18 of one of the two preformed sections 3,4, the base knot or finishing knot of a surgical knot can be formed in a simple manner.

FIGS. 15 and 16, the approximately spiral-shaped loops or similar preformed features of the preformed sections 3,4, which lie at a distance from one another, are more or less distinctly formed by straight lines 16 and curved lines or thread segments 17. Each loop of the suture material depicted in FIGS. 15 and 16 describes the approximate shape of a triangle.

However, it is also possible to form each of the spiral preformed features of sections 3,4 of the suture material as a polygon, or to provide only one preformed section in the suture material.

As can be clearly seen in FIG. 15 sections 3 4 of the thread 1 depicted there have the same direction of rotation. Two preformed sections of this type, which lie at a distance from one another and have the same direction of rotation, can be useful when the coils, loops or similar preformed features of sections 3,4 of the suture material are formed by pasting or a similar process; the pasted locations become detached when one end of the thread is pulled and the suture material is stretched in section 3 or 4. The base knot can thus be formed by means of the initial section 3, and the finishing knot can be formed by means of the other preformed section 4, for example.

Furthermore, a suture material which has two preformed sections which lie at a distance from one another and have the same direction of rotation can be used advantageously in situations where it is desirable to form merely a so-called granny knot, instead of a surgical knot. In a granny Knot, one section of the thread is knotted twice around another section of the thread. A granny knot of this type can even slip when the so-called finishing knot is formed over the base knot. If it is acceptable for the knot to be less secure while the tissue is subjected to minimal tension, this slipping of the knot can be desirable—for example, at cosmetically important sites, where it is intended to counteract the effect of excessive thread tension and the corresponding pressure exerted on the tissue. It may also be desirable in situations where sensitive tissue is involved, and excessive tension resulting from tile postoperative edema must be avoided, in order to avoid a reduction in the blood supply, delayed healing of the wound, and unfavorable scar formation.

Figure 11:
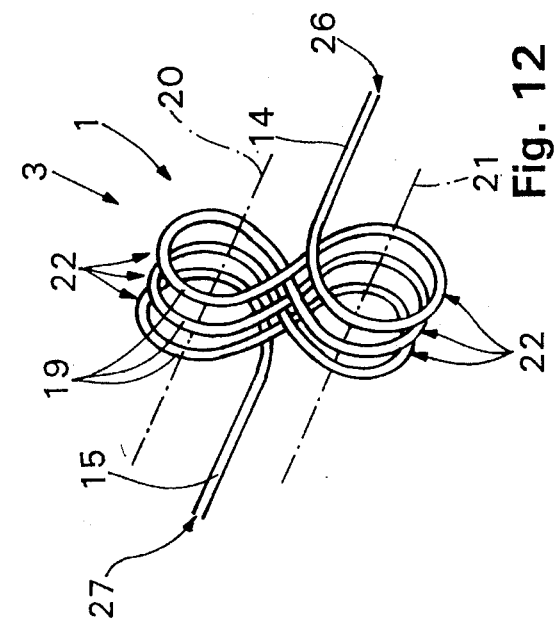
FIG. 11 is a surgical suture material similar to the one shown in FIG. 4, whose thread displays four preformed, adjacent coils or similar preformed features within one section of its length which consists of an elastic material; each of these preformed features displays an opposing direction of rotation in relation to the adjacent preformed feature; as a whole, these preformed features form two double loops with the approximate shape of a figure eight.

FIG. 11 depicts a surgical suture material whose thread 1 has four adjacent, approximately circular preformed coils 19 within one section 3 of its length, through which one of the two ends 26,27 of the thread 1 can be guided for the purpose of forming a loop and/or knot. At least one end of the thread of the suture material depicted in FIG. 11 can be connected to a needle, in a manner similar to the thread depicted in FIG. 1.

Just as in FIG. 4, each pair of two adjacent coils 19 of the suture material depicted in FIG. 11 has opposing directions of rotation. The central axes 20,21 of these adjacent, counter-rotating coils 19 lie at a distance from one another. Each pair of two adjacent coils 19 with opposing directions of rotation is arranged in approximately the same plane and form a double loop 22 with the approximate shape of a figure eight. Viewed in the same thread direction R1, the segment 23 which enters one coil 19a and the segment 24 which exits the other coil 19b are arranged on opposite sides of their common transition section 25.

The preformed section 3 depicted in FIG. 11 has only two double loops 22, so that each coil 19 of the preformed section 3 with one direction of rotation is paired with all other coil 19 with the opposing direction of rotation. This counteracts the undesirable twisting of the thread. Because of the approximate figure eight shape of the two preformed double loops 22, each pair of adjacent coils has opposing directions of rotation. The central axes 20,21 of the coils with the same direction of rotation are arranged in an approximately coaxial relationship to one another. Because of the coaxially arranged coils 19 with the same direction of rotation, the appropriate end of the thread 26,27 can be drawn through, and a base knot or finishing knot can be formed with little effort. For example, the end of the thread 26 which appears on the right in FIG. 11, on the opposite side of the preformed section 3, is inserted into the upper coils 19, which have the same direction of rotation. It is then drawn through these coils, so that a double-wound, so-called surgical base knot is formed. As soon as the base knot has been formed and the tension on the thread has been relaxed, the preformed section of elastic material—which is depicted in FIG. 11—forms anew. For the purpose of forming the finishing knot, the end of the thread can now be guided and drawn through the lower coils 19, which have a direction of rotation opposite to that of the upper coils. This forms a so-called sailor's knot, whose base and finishing knots—which are tied in opposite directions—are known to guarantee an especially secure seat for the overall knot.

On the other hand, if the finishing knot is intended to be wound only once, the end of the thread 26 is guided through only one of the two lower coils 19.

In order to form the base knot as a double-wound surgical knot and then execute merely a single-wound finishing knot, for example, it is also sufficient to employ an embodiment in which the preformed section of the suture material displays three adjacent coils 19, of which one coil 19 of a certain direction of rotation is enclosed between two coils 19 of the opposing direction of rotation.

On the other hand, if the conditions require a seat which will slip, in the form of a so-called granny knot, the appropriate end of the thread 26 must be pulled through the same coils 19 in the direction of the arrow R2, in order to form the base knot and finishing knot.

Figure 12:
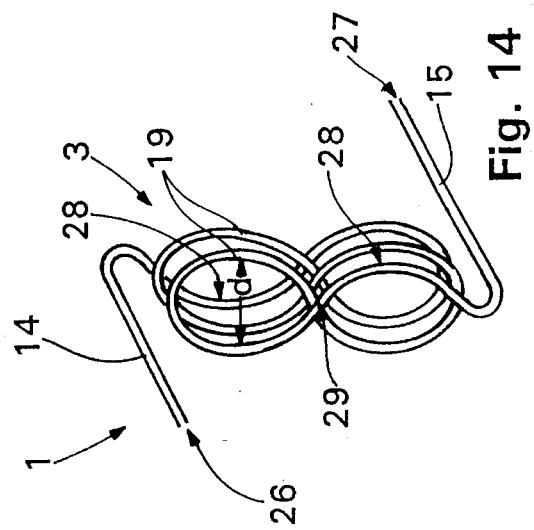
FIG. 12 is the thread of a surgical suture material with three double loops having the approximate shape of a figure eight.

FIG. 12 depicts a surgical suture material whose thread 1 has three double loops 22. These three double loops 22 are formed from six adjacent, circular preformed coils, loops or similar preformed features 19. Each pair of adjacent preformed features has opposing directions of rotation. Each pair of two adjacent coils 19 with opposing directions of rotation is arranged in approximately the same plane and forms one of the double loops 22 with the approximate shape of a figure eight. In this case, the central axes 20,21 of the three coils 19 with the same direction of rotation are also arranged in an approximately coaxial relationship to one another. The preformed section 3 of the thread 1 depicted in FIG. 12 creates a variety of possibilities for the formation of knots. For example, if one end of the thread 26,27 on the opposite side is drawn through all three coils with the same direction of rotation, a thrice-wound, relatively secure base knot is formed. The individual double loops 22 lie at a slight distance from one another, so that it also possible to use only one coil 19 or two coils 19 with the same direction of rotation to form the knot in a simple manner.

For the purpose of threading one end of the thread through these preformed features 19, it is useful for the coil 19 or coils 19 of at least one direction of rotation to have an inside diameter d which at least corresponds to the thickness of the thread or end of the thread which is to be guided through the preformed features. Even if the other coil 19 with the opposing direction of rotation has a smaller diameter, through which it is difficult to guide one of the two ends of the suture material, the undesirable twisting of the surgical suture material—and especially its thread 1—is still counteracted during the formation of the knot. As shown here, it is useful for all coils 19 of the preformed section 3 to have a diameter d through which the jaw parts of a needle holder or thread holder can be guided, so that the thread holder can be used to grasp the appropriate end of the thread 26,27 through the coils 19 for the purpose of forming the knot.

It is also possible to form the thread with three adjacent, circular preformed coils 19, for example. Here the coils 19 are arranged in approximately the same plane, and adjacent coils 19 have opposing directions of rotation. It is also possible for the suture material to extend directly from two coils 19 with opposing directions of rotation to a coil 19 which has the same direction of rotation as at least one of the coils 19 to which it is adjacent. Even embodiments of this type counteract the undesirable twisting of the suture material provided by the invention—and especially its thread 1. However, embodiments of this type can not completely prevent such twisting, because not every coil 19 of the preformed section 3 with a given direction of rotation is paired with another coil 19 with the opposing direction of rotation.

Figure 13:
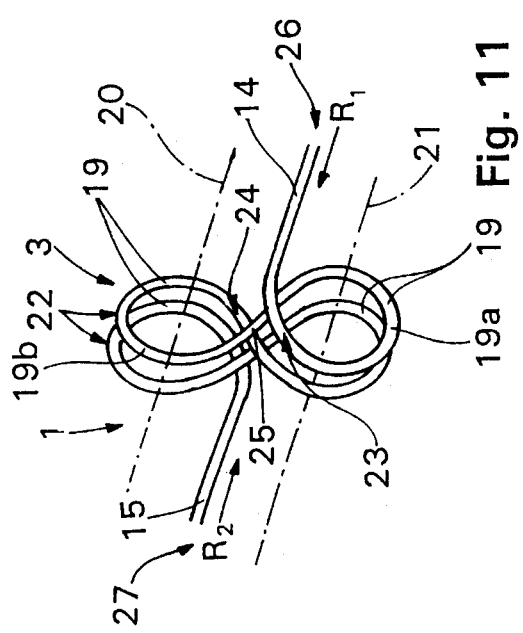
FIG. 13 is the thread of a surgical suture material similar to those shown in FIGS. 4, 11 and 12; in the region of the outer ends of the figure-eight-shaped double loops, both segments of the thread which are adjacent to the preformed sections are angled in an approximately perpendicular relationship to the plane formed by the adjacent coils.

In FIGS. 11 through 14, both of the thread segments 14,15 which are adjacent to the preformed coils 19 are angled in a direction which is perpendicular to the plane which extends parallel to the adjacent coils 19 and the double loops 22. In FIGS. 11 and 12, the outer coils 19 are directly adjacent to the angled thread segments 14,15. In FIGS. 13 and 14, each of the outer coils 19 is adjacent to a semicircular coil or curve 28 with the opposing direction of rotation. The approximately perpendicularly angled thread segment 14,15 is then adjacent to this curve on the side of the curve 28 which is directed away from the transition section 29, which in turn is provided between the coil 19 and the curve 28.

The sections 3 depicted in FIGS. 13 and 14 allow a faster determination of the positions of the coils, loops or similar preformed features 19 and the adjacent ends of the thread 26 and 27. This further facilitates a simpler manipulation of the thread and the overall suture material.

The thread segments 14,15, which are adjacent to the preformed coils 19 in FIG. 14, are angled in an approximately perpendicular relationship to the adjacent preformed section 3 outside the coils 19. This can make it considerably simpler to guide an end of the thread 26,27 through the corresponding coils 19 on the opposite side. In particular, it allows a needle holder or thread holder to be guided from the side which is located away from the seat of the knot through the preformed section of the suture material, for example, so that the other end of the thread can then be drawn through. This can be helpful in accomodating the vertical position of the instruments in endoscopic operations and reducing the amount of space required for the instrument motions. Furthermore, the threads depicted in FIGS. 13 and 14 are also formed with two preformed double loops 22 with the approximate shape of a figure eight, similar to FIG. 11.

On the other hand, FIG. 4 depicts the thread 1 of a surgical suture material in which the coils, loops or similar preformed features 19 of the preformed section 3 and the adjacent thread segments 14,15 are arranged in approximately the same plane. Therefore, this surgical suture material assumes a relatively flat form. In the case of the suture material depicted in FIG. 4, it also true that a curve 28 is provided on each side of the preformed section 3. This curve displays a direction of rotation which opposes that of the adjacent coil, loop or similar preformed feature 19. Because the preformed section 3 of the suture material depicted in FIG. 4 is essentially formed from two double loops 22, which are adjacent to another circular coil or loop 19 on one side, the thread segments 14,15 which are adjacent to the preformed section 3 are arranged on the same side along the length of this section 3.

If the preformed section of the suture material according to the invention consists of elastic material which returns to its original, approximate figure eight shape or similar preformed shape without the influence of a tensile load, the suture material can first be drawn through a trocar cannula or the tissue which is to be sutured, even when the diameter of the preformed section is greater than the inside diameter of a trocar cannula. It is then possible for at least sections of the suture material to assume the figure eight shape, eyeglass shape, or similar preformed shaped which is desired for tying the knot. Therefore, the surgical suture material depicted in FIGS. 1 through 16 in various embodiments can be used not only in operations on the open abdomen or in skin sutures, but also in intracorporeal endoscopic operations in particular.

The sections 3 of the coils, loops or similar preformed features 19 of the suture materials depicted in FIG. 4 and FIGS. 11 through 14 can also be preformed by pasting or a similar process. In order to also be able to form a double knot—with a base knot and a finishing knot—an embodiment of this type, it can be useful for the suture materials which are depicted in FIG. 4 and FIGS. 11 through 14 to display two preformed sections which lie at a distance from one another and in turn display double loops 22 in the form of figure eights.

As a result of the approximately perpendicular angled position of the thread segments 5, 14 and 15 which are adjacent to the preformed sections 3,4 in FIGS. 1 and 2 and FIGS. 5 through 16, the coils, loops or similar preformed features 19 of these preformed sections 3,4 form a thread opening which is arranged in a practically transverse relationship to the longitudinal axis of the suture material. The two jaw parts of a conventional thread holder or needle holder or the end of the thread which is to be guided through the coils can be guided through this thread opening in a simple manner. This makes it considerably easier to form knots—even in situations where space is limited. In order to be able to clearly recognize the direction of rotation of the appropriate windings of the preformed section, and in order to be able to estimate the position of this preformed section 3 and/or 4—even when the suture material is stretched straight—it is practical for the coils or similar preformed features of at least one direction of rotation to display a marking dye, marking coating or similar form of marking.

Figure 17:
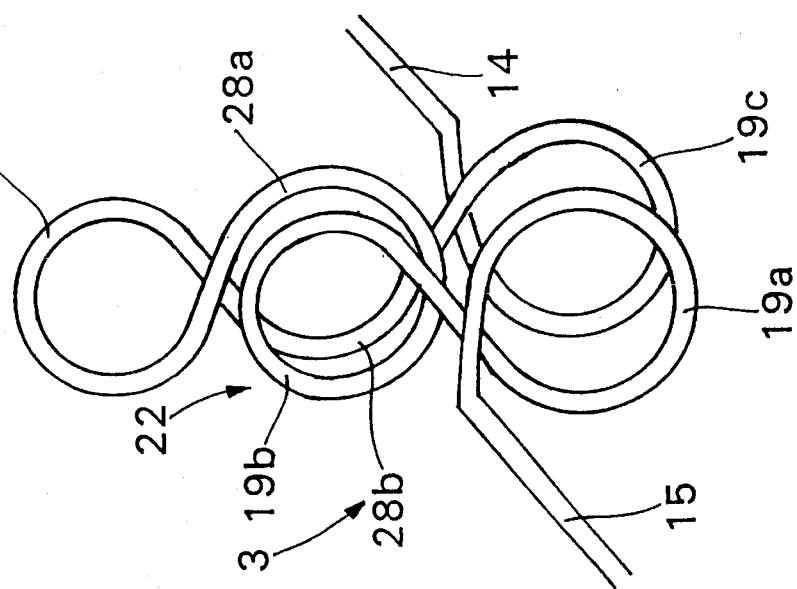
FIG. 17 is a section formed from two double loops, in which these double loops are displaced in relation to one another.
Figure 18:
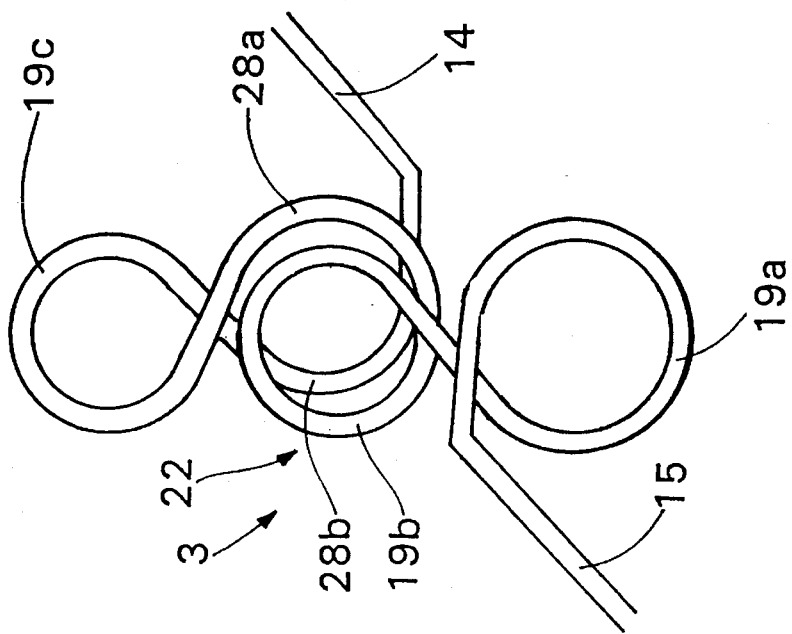
FIG. 18 is the preformed section of a suture material; this section essentially displays a double loop and an adjacent preformed feature consisting of three loops.

FIGS. 17 and 18 depict two preformed sections 3 of a surgical suture material which are only slightly different from one another but are intended to be used for different purposes.

Each of the preformed sections 3 depicted in FIGS. 17 and 18 displays a double loop 22 with the approximate shape of a Figure eight. The double loop is formed from an initial coil, loop or similar preformed feature 19a and a second preformed feature 19b with an opposing direction of rotation. This second preformed feature 19b of the double loop 22 is adjacent to an initial curve 28a with the same direction of rotation. A third coil, loop or similar preformed feature 19c, with a direction of rotation which opposes that of the initial curve 28a, is adjacent to this initial curve 28a on the side of the curve which is directed away from the second preformed feature 19b. For its part, this third preformed feature 19c is adjacent to a second curve 28b with an opposing direction of rotation. The arc-shaped curves 28a, 28b form the outline of a fourth loop, whose loop opening practically overlaps the loop opening of the second preformed feature 19b. The central axes of the first, second and third preformed features 19a, 19b, and 19c lie at a distance from one another, are parallel to one another, and proceed in practically the same plane. The central axis of the fourth preformed feature, which is formed by the curves 28a and 28b, is arranged in an approximately coaxial relationship to the central axis of the second preformed feature 19b.

In the section 3 depicted in FIG. 17, the thread segment 14 which exits the second curve 28b is angled in an approximately perpendicular manner and also runs parallel to the central axes of the preformed features 19, while in the section 3 depicted in FIG. 18, a fifth coil, loop or similar preformed feature 19e is adjacent to the second curve 28b and has a direction of rotation which opposes that of the curve 28b. This loop 19e, whose central axis is arranged in an approximately coaxial relationship to the central axis of the initial preformed feature 19a, and the fourth preformed feature—which in turn is formed by the curves 28a and 28b and the third preformed feature 19c form a thread segment consisting of three loops.

The marking described above can be omitted in the preformed section 3 depicted in FIG. 17. The preformed section 3 depicted in FIG. 17 allows a surgical base knot with a simple finishing knot to be formed as a sailor's knot in a simple manner, for example. For example, this can be accomplished by guiding the end of the thread through the middle opening of the preformed feature which is formed by the curves 28a and 28b and through the coil 19b in order to form the base knot, and then through one of the two outer openings of the preformed features 19a and 19c in order to form the finishing knot. Because the relative positions of the three openings in the preformed section 3—which lie at a distance from one another—allow one to recognize the orientation with certainty, the marking of the coils can be omitted in the embodiment depicted in FIG. 17.

On the other hand, a secure, sturdy knot can even be formed with the section 3 depicted in FIG. 18 when using a stiff suture material which has an especially smooth surface, which in turn results in a low adhesive friction in the region where the knot is seated. It then becomes easy to form a surgical knot with a section 3 of the suture material which is formed as depicted in FIG. 18, for example. This surgical knot can be secured with a second, surgically formed sailor's knot. For its part, this second knot can then be further secured by another simple sailor's knot. A double-secured surgical knot of this type is often used in operations on the open abdomen, especially when using the above-mentioned thread with an especially smooth surface. Within the context of an intracorporeal endoscopic operation, a knot of this type can only be achieved with great skill and a considerable amount of time when using the thread material which has been available until now.

As shown in FIGS. 17 and 18, the intersecting segments of the transition sections formed by the loops 19 or curves 28 are displaced in relation to one another in a regular, sequential arrangement in one direction along the length of the thread or suture material.

An embodiment of the invention which is not depicted here provides for the suture material to be formed in two or more parts. The preformed section or sections 3,4 and the thread segment 5 which lies between them—consisting of elastic material, for example—form one part, while at least one of the two thread segments 14,15 which are adjacent to sections 3,4 forms another part of this multi-part suture material. The preformed sections 3,4 and the adjacent thread segments—which may also consist of inelastic material in some cases—can be connected to one another in a detachable manner by means of a plug connection, clamp connection or similar connecting element. In particular, a connecting element which can be detachably connected with the thread 1 of the suture material according to the invention allows the preformed sections to be used repeatedly and connected with thread material which in some cases consists of a material which is inelastic, and especially compatible with the tissue. This may be in contrast to the preformed sections 3,4 of the suture material, which can be removed after the knot has been formed, for example. It is also possible for the thread and/or at least one of the preformed sections 3,4 of the suture material to be made of a memory metal, especially a nickel-titanium alloy. Sections of this alloy can return from their elongated form—in which they can easily be guided through a trocar cannula—to their preformed shape. This return can occur in a temperature-dependent manner, for example.

While it is possible to form a knot by using spirals which consist of only one winding, or even by using only one double loop, spirals with multiple windings or multiple double loops are preferred in practice. This secures the holding function and strength of the knot which has been formed with the suture material according to the invention.

The suture material can take the form of continuous lengths with thread segments 5 which are not preformed lying between preformed sections 3,4 with alternating directions of rotation. This makes the manufacture of the suture material especially cost-effective. However, it is also possible to package the suture material with only one thread 1 and an attached needle 2, This facilitates the quick and secure manipulation of the suture material and also ensures its sterility.

The present invention may be embodied in other specific forms without departing from the spirit or essential attributes thereof and, accordingly, reference should be made to the appended claims, rather than to the foregoing specification as indicating the scope of the invention.

We claim:

1. Surgical suture material comprising a length of surgical thread having at least two initial preformed sections in spaced relationship to each other along its length, a free thread end extending from one side of one of said preformed sections and an opposite thread end extending from an opposite side of said another of said preformed sections, each said preformed section comprising a preformed feature having at least one inherently stable loop, said at least one loop of one preformed section having a direction of rotation opposing a direction of rotation of said at least one loop in another preformed section, such that when the free thread and is guided through a preformed feature from an opposite side of a preformed section and the ends are pulled away from each other, a knot is automatically formed in the thread.

2. Surgical suture material in accordance with claim 1 wherein at least one preformed section of the suture material is formed as a preformed feature with an approximately spiral shape.

3. Surgical suture material in accordance with claim 2 wherein the suture material has multiple preformed sections, each preformed section having a preformed feature with an approximately spiral shape, the spiral preformed features of adjacent spaced apart preformed sections having opposing directions of rotation.

4. Surgical suture material in accordance with claim 2 wherein the spiral preformed feature of at least one section of the suture material has multiple loops.

5. Surgical suture material in accordance with claim 2 wherein the spiral preformed section of the suture material has an inside diameter (d) slightly larger than the diameter of the thread material, for the purpose of threading the free thread end through it.

6. Surgical suture material in accordance with claim 1 wherein the suture material has at least two adjacent preformed features in at least one initial preformed section of its length, said preformed features having opposing directions of rotation, said adjacent, counter-rotating preformed features having central axes which lie at a distance from one another.

7. Surgical suture material in accordance with claim 6 wherein each pair of two adjacent preformed features with opposing directions of rotation is arranged in approximately the same plane.

8. Surgical suture material in accordance with claim 6 wherein each of the two adjacent preformed features with opposing directions of rotation has the form of a double loop with an approximate shape of a figure eight.

9. Surgical suture material in accordance with claim 8 wherein the suture material has two preformed sections which lie at a distance from one another, and whose figureeight-shaped preformed features have double loops with opposing directions of rotation.

10. Surgical suture material in accordance with claim 6 wherein a segment of suture material which leads to one of the preformed features and a segment of suture material which follows from the other preformed feature are arranged on opposite sides of a common transition section between the preformed features.

11. Surgical suture material in accordance with claim 6 wherein each preformed feature of the preformed section with a given direction of rotation is paired with another preformed feature with an opposing direction of rotation.

12. Surgical suture material in accordance with claim 6 wherein the preformed section of the suture material has more than two adjacent preformed features, adjacent preformed features having opposing directions of rotation, and wherein preformed features with the same direction of rotation have central axes arranged in an approximately coaxial relationship to one another.

13. Surgical suture material in accordance with claim 6 wherein the preformed section of the suture material has three adjacent preformed features, one preformed feature with a given direction of rotation being enclosed between two preformed features with the opposing direction of rotation.

14. Surgical suture material in accordance with claim 6 wherein at least one preformed feature of the preformed section is adjacent to a semicircular curve with an opposing direction of rotation, a segment of the suture material which is adjacent to the preformed section being angled on a side of the curve which is directed away from a transition section, which in turn is provided between the preformed feature and the curve.

15. Surgical suture material in accordance with claim 1 wherein at least one segment of the suture material which is adjacent to at least one preformed section is angled in a transverse relationship to a plane which is formed by adjacent preformed features.

16. Surgical suture material in accordance with claim 1 wherein a segment of the suture material outside at least one preformed feature is angled in the direction of an adjacent preformed section.

17. Surgical suture material in accordance with claim 1 wherein two adjacent similar preformed features with opposing directions of rotation are arranged in an eyeglass shape in relation to one another.

18. Surgical suture material in accordance with claim 17 wherein a segment of suture material which leads to one preformed feature and a segment of suture material which follows from the other preformed feature are arranged on the same side of a common transition section.

19. Surgical suture material in accordance with claim 1 wherein a marking is displayed in selected areas at least one preformed sections of the suture material.

20. Surgical suture material in accordance with claim 1 wherein at least one preformed section has a longitudinal axis arranged in the longitudinal direction of the suture material.

21. Surgical suture material in accordance with claim 1 wherein at least the preformed sections of the suture material comprise elastic material.

22. Surgical suture material in accordance with claim 1 wherein a segment of the suture material which is not preformed is arranged between the preformed sections, which lie in spaced relationship with one another.

23. Surgical suture material in accordance with claim 1 wherein one of the thread ends has a needle attached thereto.

24. Surgical suture material in accordance with claim 1 wherein at least one preformed section of the suture material is formed as a piece which is detachably connected to an adjacent segment of thread.

25. Surgical suture material in accordance with claim 1 wherein at least a portion of the thread comprises a memory metal.

26. Surgical material in accordance with claim 1 wherein at least one preformed section has a double loop with the approximate shape of a figure eight, which is formed from an initial preformed feature and a second preformed feature with an opposing direction of rotation, the section preformed feature of said double loop being adjacent to an initial curve in the suture material with the same direction of rotation, a section of the double loop which is directed away from the initial preformed feature having an initial curve adjacent to a third preformed feature with a direction of rotation which opposes that of the initial curve, a second being adjacent to the third preformed feature with an opposing direction of rotation, and said initial and second curves forming an outline of a fourth preformed feature having a loop opening overlapping a loop opening of the second preformed feature in at least certain regions.

27. Surgical suture material in accordance with claim 26 further comprising a fifth preformed feature adjacent to the second curve with an opposing direction of rotation.

28. Surgical suture material in accordance with claim 26 wherein central axes of the preformed features lie in approximately parallel directions, the central axes of the second and fourth preformed features being arranged in an approximately coaxial relationship to one another.

29. Surgical suture material in accordance with claim 1 comprising plural preformed features having intersecting segments which are displaced in relation to one another in a regular, sequential arrangement in one direction along the length of the suture material.

* * * * *